US011268081B2

(12) United States Patent
Thomas et al.

(10) Patent No.: US 11,268,081 B2
(45) Date of Patent: Mar. 8, 2022

(54) IMPROVING EXPRESSION OF A PROTEASE BY CO-EXPRESSION WITH PROPEPTIDE

(71) Applicant: Novozymes A/S, Bagsvaerd (DK)

(72) Inventors: Michael Thomas, Davis, CA (US); Steen Joergensen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/652,937

(22) PCT Filed: Oct. 18, 2018

(86) PCT No.: PCT/US2018/056578
§ 371 (c)(1),
(2) Date: Apr. 1, 2020

(87) PCT Pub. No.: WO2019/083818
PCT Pub. Date: May 2, 2019

(65) Prior Publication Data

US 2020/0263156 A1 Aug. 20, 2020

Related U.S. Application Data

(60) Provisional application No. 62/575,911, filed on Oct. 23, 2017.

(51) Int. Cl.
*C12N 9/54* (2006.01)
*C12N 15/67* (2006.01)
*C12P 21/02* (2006.01)

(52) U.S. Cl.
CPC ............... *C12N 9/54* (2013.01); *C12N 15/67* (2013.01); *C12P 21/02* (2013.01)

(58) Field of Classification Search
None
See application file for complete search history.

(56) References Cited

FOREIGN PATENT DOCUMENTS

WO 2006042548 A1 4/2006
WO 2014206829 A1 12/2014

OTHER PUBLICATIONS

Chang et al. Secretion of Active Subtilisin YaB by a Simultaneous Expression of Separate Pre-pro and Pre-mature Polypeptides in Bacillus subtilis. Biochemical and Biophysical Research Communications 219, 463-468 (1996) (Year: 1996).*
Cao et al, 2000, The J of Biological Chem 275(38), 29648-29653.
Liu et al, 2011, Micro Cell Fac 10, 112.
Mansfeld et al, 2005, Prot Expres Purif 39(2), 219-228.
Marie-Claire et al, 1999, J Mol Biol 285(5), 1911-1915.
Meyer et al, 2016, The J of Biological Chem 291(37), 19449-19461.
Nickerson et al, 2008, Mol Microbiol 69(6), 1530-1543.
Safina et al, 2011, Protein and Peptide letters 18(11), 1119-1125.
Schlatter(Ed), 2016, Physics letters B 760, 647-665.
Yasukawa et al, 2007, Protein engineering, design and selection 20(8), 375-383.

* cited by examiner

*Primary Examiner* — Kagnew H Gebreyesus
(74) *Attorney, Agent, or Firm* — Eric Fechter

(57) ABSTRACT

The present invention relates to prokaryotic host cells and methods for improving expression of a mature protease by co-expression with a propeptide of said protease as two separate polypeptides.

20 Claims, 7 Drawing Sheets

Specification includes a Sequence Listing.

IMPROVING EXPRESSION OF A PROTEASE BY CO-EXPRESSION WITH PROPEPTIDE

CROSS-REFERENCE TO RELATED APPLICATIONS

This application is a 35 U.S.C. 371 national application of PCT/US2018/056578, filed Oct. 18, 2018, which claims priority or the benefit from U.S. Provisional Patent Application No. 62/575,911, filed Oct. 23, 2017. The contents of these applications are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to methods for improving expression of a protease proenzyme comprising a mature protease by co-expression with a propeptide of said mature protease as two separate polypeptides. The present invention also relates to prokaryotic host cells having a genome comprising the elements suitable for such improved expression.

BACKGROUND OF THE INVENTION

Enzymes and other bioactive polypeptides derived from naturally occurring organisms are interesting molecules from both scientific and commercial perspective. Once such a polypeptide product has been identified, efforts are often made to develop optimized manufacturing methods for improved production of the polypeptide in question.

We have observed that co-expression of two different proteases, namely *Pyrococcus furiosus* Protease S (PfuS) and *Bacillus horneckiae* Protease S8A (BH-S8A) together with their respective propeptides as separate polypeptides results in markedly improved expression of both PfuS and BH-S8A. Based on this finding, we propose that co-expression of a protease with a propeptide as two separate polypeptides may be useful for improving expression of proteases in general.

SUMMARY OF THE INVENTION

The present invention is based on the surprising finding that co-expression of a protease proenzyme comprising a mature protease together with propeptide of said protease as two separate polypeptides results in a markedly increased expression of the mature protease.

Thus, in a first aspect, the present invention relates to a prokaryotic host cell comprising in its genome at least one polynucleotide encoding a protease proenzyme comprising a mature protease and at least one polynucleotide encoding a propeptide of said mature protease, wherein the polynucleotide encoding the protease proenzyme and the polynucleotide encoding the propeptide are not expressed as a translationally fused protein.

In a second aspect, the present invention relates to a method for producing a mature protease, the method comprising:

a. providing a prokaryotic host cell as defined in the first aspect;
b. cultivating said prokaryotic host cell under conditions conducive for expression of the mature protease; and, optionally,
c. recovering the mature protease.

DEFINITIONS

Figure 1:
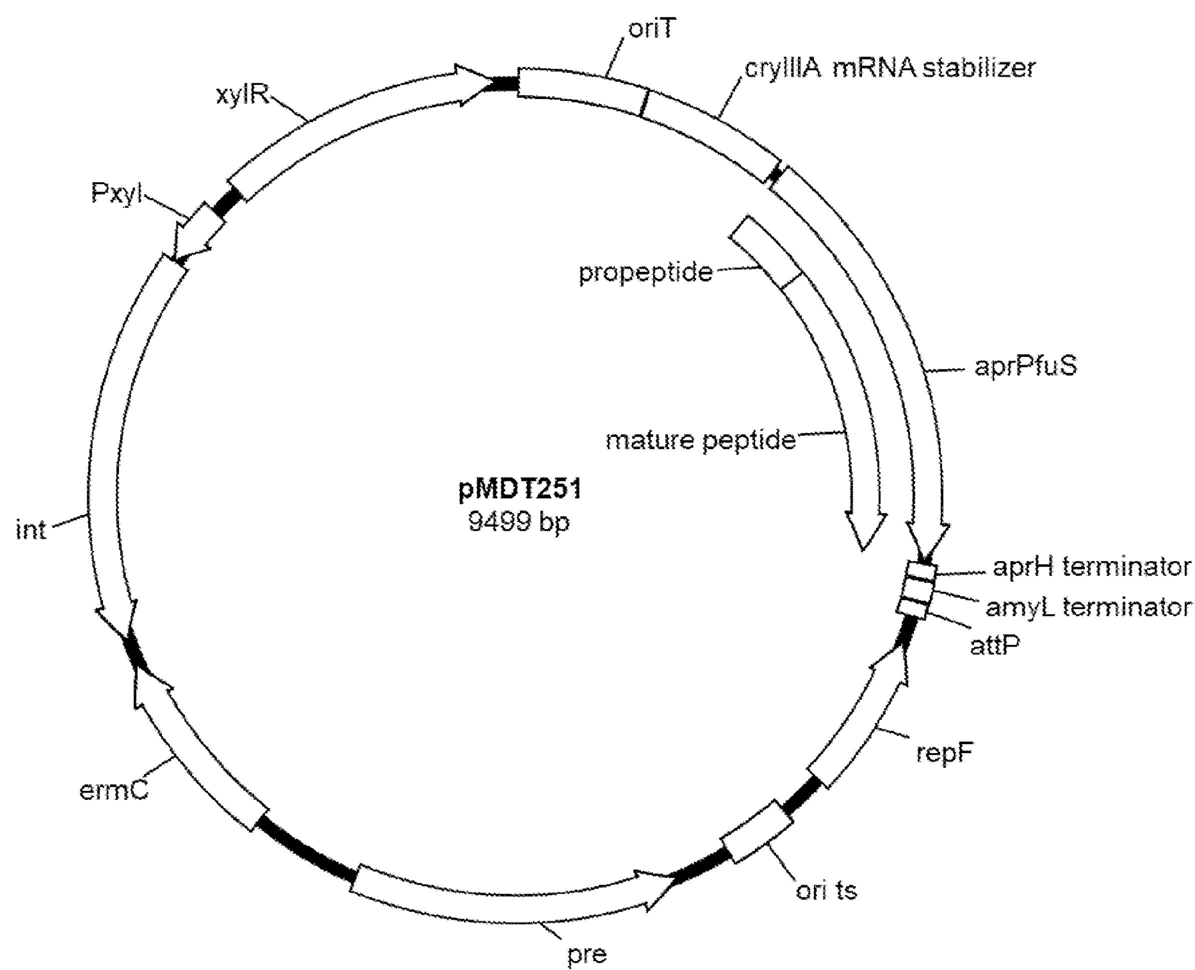
FIG. 1 shows a plasmid map of pMDT251, which comprises the aprPfuS gene flanked upstream by the cryIIIA mRNA stabilizer region and downstream by the attP site of lactococcal bacteriophage TP901-1, and was introduced into conjugation donor strain *Bacillus subtilis* PP3724 by transformation, resulting in strain PP3724/pMDT251, as described in Example 1.

Expression: The term "expression" includes any step involved in the production of a polypeptide including, but not limited to, transcription, post-transcriptional modification, translation, post-translational modification, and secretion.

Mature polypeptide coding sequence: The term "mature polypeptide coding sequence" means a polynucleotide that encodes a mature polypeptide having protease activity.

Operably linked: The term "operably linked" means a configuration in which a control sequence is placed at an appropriate position relative to the coding sequence of a polynucleotide such that the control sequence directs expression of the coding sequence.

Protease proenzyme: The term "protease proenzyme" means an inactive or partially active protease precursor, comprising a propeptide and a mature protease, such that the protease is activated by cleavage of the propeptide, releasing the active mature protease.

Sequence identity: The relatedness between two amino acid sequences or between two nucleotide sequences is described by the parameter "sequence identity". For purposes of the present invention, the sequence identity between two amino acid sequences may be determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used may be, e.g., gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences may be determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used may be, e.g., gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Variant: In the context of a mature protease, the term "variant" means a polypeptide having protease activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g., several) amino acids, e.g., 1-5 amino acids, adjacent to and immediately following the amino acid occupying a position.

In the context of a propeptide, the term "variant" means a polypeptide having propeptide activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g., several) amino acids, e.g., 1-5 amino acids, adjacent to and immediately following the amino acid occupying a position.

The term "propeptide activity" may refer to any function of a propeptide in the context of prokaryotic protease expression, including, but not limited to, maintaining the protease in an inactive state prior to secretion to avoid intracellular proteolysis, promoting correct folding of the protease, altering protease specificity, and acting as membrane anchor (as described in, e.g., Wandersman, 1989, *Mol. Microbiol.* 3: 1825-1831).

DETAILED DESCRIPTION OF THE INVENTION

The present invention is based on the surprising finding that co-expression of a protease proenzyme comprising a mature protease and a propeptide of said mature protease as two separate polypeptides results in a markedly improved expression of the mature protease. As can be seen from the Examples enclosed herein, co-expression of the *Pyrrococcus furiosus* Protease S (PfuS) proenzyme and the PfuS propeptide improves expression of PfuS both in terms of titer and total product. Likewise, co-expression of the *Bacillus horneckiae* Protease S8A (BH-S8A) proenzyme and the BH-S8A propeptide improves expression of BH-S8A in terms of titer levels. Given the constant aspiration to improve production methods for commercially relevant enzymes, the present invention is highly relevant and addresses an unmet need in the art.

Thus, in a first aspect, the present invention relates to a prokaryotic host cell comprising in its genome at least one polynucleotide encoding a protease proenzyme comprising a mature protease and at least one polynucleotide encoding a propeptide of said mature protease, wherein the at least one polynucleotide encoding the protease proenzyme and the at least one polynucleotide encoding the propeptide are not expressed as a translationally fused protein.

Prokaryotic Host Cells

The prokaryotic host cell may be any cell useful in the recombinant production of a mature protease of the present invention. The term "host cell" encompasses any progeny of a parent cell that is not identical to the parent cell due to mutations that occur during replication.

The prokaryotic host cell is a Gram-positive bacterial host cell. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*.

Preferably, the prokaryotic host cell may be any *Bacillus* cell. More preferably, the prokaryotic host cell may be selected from the group consisting of *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis* cells. Even more preferably, the prokaryotic host cell is a *Bacillus licheniformis* host cell.

The prokaryotic host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The prokaryotic host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

Polynucleotides

The prokaryotic host cell of the invention comprises in its genome at least one polynucleotide encoding a protease proenzyme comprising a mature protease and at least one polynucleotide encoding a propeptide of said mature protease. Preferably, the number of polynucleotides encoding the protease proenzyme and the number of polynucleotides encoding the propeptide are, independently, up to three, e.g., 1, 2, or 3. More preferably, the number of polynucleotides encoding a protease and the number of polynucleotides encoding the propeptide of said protease are, independently, up to six, e.g., 1, 2, 3, 4, 5, or 6. Most preferably, the number of polynucleotides encoding a protease and the number of polynucleotides encoding the propeptide of said protease are, independently, up to ten, e.g., 1, 2, 3, 4, 5, 6, 7, 8, 9, or 10.

The present invention relates to polynucleotides encoding any protease proenzyme comprising a mature protease. In a preferred embodiment, the at least one polynucleotide encoding a protease proenzyme comprises a polynucleotide encoding a mature protease that has a sequence identity to the mature polypeptide coding sequence of SEQ ID NO:1 of at least 80%, e.g., at least 85%, at least 90%, at least 91%, at least 92%, at least 93%, at least 94%, at least 95%, at least 96%, at least 97%, at least 98%, at least 99%, or 100%. Also in a preferred embodiment, the at least one polynucleotide encoding a protease proenzyme comprises a polynucleotide encoding a mature protease that has a sequence identity to the mature polypeptide coding sequence of SEQ ID NO:5 of at least 80%, e.g., at least 85%, at least 90%, at least 91%, at least 92%, at least 93%, at least 94%, at least 95%, at least 96%, at least 97%, at least 98%, at least 99%, or 100%.

Likewise, the present invention relates to polynucleotides encoding a propeptide of any protease. In a preferred embodiment, the at least one polynucleotide encoding a protease propeptide has a sequence identity to SEQ ID NO:3 of at least 80%, e.g., at least 85%, at least 90%, at least 91%, at least 92%, at least 93%, at least 94%, at least 95%, at least 96%, at least 97%, at least 98%, at least 99%, or 100%. Also in a preferred embodiment, the at least one polynucleotide encoding a protease propeptide has a sequence identity to SEQ ID NO:7 of at least 80%, e.g., at least 85%, at least 90%, at least 91%, at least 92%, at least 93%, at least 94%, at least 95%, at least 96%, at least 97%, at least 98%, at least 99%, or 100%.

The present invention also relates to isolated polynucleotides encoding a protease proenzyme and a propeptide, as described herein.

The techniques used to isolate or clone a polynucleotide are known in the art and include isolation from genomic DNA or cDNA, or a combination thereof. The cloning of a polynucleotide from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotide may be cloned from a strain of *Pyrrococcus* or *Bacillus*, or related organisms and thus, for example, may be an allelic or species variant of the polypeptide encoding region of the polynucleotide.

Modification of a polynucleotide encoding a protease proenzyme and/or a propeptide of the present invention may be necessary for synthesizing polypeptides substantially similar to mature proteases and/or propeptides of the invention. The term "substantially similar" refers to non-naturally occurring forms of such protease proenzymes and/or propeptide. The protease proenzyme and propeptide may differ in some engineered way from the protease proenzyme and propeptide isolated from their native source, e.g., variants that differ in specific activity, thermostability, pH optimum, or the like. The protease proenzyme and propeptide variants may be constructed on the basis of the polynucleotides presented as the mature polypeptide coding sequence of SEQ ID NO:1 and SEQ ID NO:3, respectively, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising at least one polynucleotide encoding a protease proenzyme comprising a mature protease and at least one polynucleotide encoding a propeptide of said mature protease operably linked to one or more control sequences that direct the expression of the coding sequence in a suitable host cell under conditions compatible with the control sequences.

The polynucleotides may be manipulated in a variety of ways to provide for expression of the protease proenzyme and propeptide. Manipulation of the polynucleotides prior to their insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a protease proenzyme and/or propeptide of the present invention. The promoter contains transcriptional control sequences that mediate the expression of the protease proenzyme and/or propeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

In an embodiment, the at least one polynucleotide encoding a protease proenzyme of the invention and the at least one polynucleotide encoding a propeptide have been integrated into same locus or different loci in the genome of the prokaryotic host cell.

Preferably, the at least one polynucleotide encoding a protease proenzyme and the at least one polynucleotide encoding a propeptide are each operably linked with a separate promoter; preferably, the separate promoters are identical copies of the same promoter.

Alternatively, the at least one polynucleotide encoding a protease proenzyme and the at least one polynucleotide encoding a propeptide are operably linked with a promotor in an operon.

Examples of suitable promoters for directing transcription of the nucleic acid constructs of the present invention in a prokaryptic host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIII A gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a prokaryotic host cell to terminate transcription. The terminator is operably linked to the 3'-terminus of the polynucleotide encoding a protease proenzyme and/or propeptide. Any terminator that is functional in the prokaryotic host cell may be used in the present invention.

Preferred terminators for prokaryotic host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a signal peptide coding region that encodes a signal peptide linked to the N-terminus of a mature protease of the invention and directs the mature protease into the cell's secretory pathway. The 5'-end of the coding sequence of the polynucleotide encoding the protease proenzyme may inherently contain a signal peptide coding sequence naturally linked in translation reading frame with the segment of the coding sequence that encodes the mature protease. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the mature protease. However, any signal peptide coding sequence that directs the expressed mature protease into the secretory pathway of a host cell may be used.

Effective signal peptide coding sequences for prokaryotic host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a mature protease of the invention. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the protease proenzyme and/or propeptide relative to the growth of the prokaryotic host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. Other examples of regulatory sequences are those that allow for gene amplification.

Expression Vectors

The present invention also relates to recombinant expression vectors comprising at least one polynucleotide encoding a protease proenzyme comprising a mature protease, at least one polynucleotide encoding a propeptide of said mature protease, a promoter, and transcriptional and translational stop signals. The various polynucleotides and control sequences may be joined together to produce a recombinant expression vector that may include one or more convenient restriction sites to allow for insertion or substitution of the polynucleotide encoding a protease and/or the polynucleotidence encoding a propeptide of said protease at such sites. Alternatively, the polynucleotides may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotides. The choice of the vector will typically depend on the compatibility of the vector with the prokaryotic host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the prokaryotic host cell, is integrated into the genome and replicated together with the chromosome(s) into which it has been integrated. Furthermore, a single vector or plasmid or two or more vectors or plasmids that together contain the total DNA to be introduced into the genome of the prokaryotic host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance.

The vector preferably contains an element(s) that permits integration of the vector into the genome of the prokaryotic host cell or autonomous replication of the vector in the cell independent of the genome.

For integration into the prokaryotic host cell genome, the vector may rely on the polynucleotides encoding the protease and/or propeptide or any other element of the vector for integration into the genome by homologous or nonhomologous recombination. Alternatively, the vector may contain additional polynucleotides for directing integration by homologous recombination into the genome of the prokaryotic host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the prokaryotic host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a prokaryotic host cell. The term "origin of replication" or "plasmid replicator" means a polynucleotide that enables a plasmid or vector to replicate in vivo.

Examples of prokaryptic origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

As alluded to above, more than one copy of a polynucleotide encoding a protease proenzyme comprising a mature protease and a polynucleotide encoding a propeptide of said mature protease may be inserted into a prokaryotic host cell to increase production of the mature protease. An increase in the copy number of the polynucleotides can be obtained by integrating at least one additional copy of the polynucleotide sequence into the prokaryotic host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well-known to one skilled in the art (see, e.g., Sambrook et al., 1989, supra).

Mature Proteases and Propeptides

The mature protease of the invention may be any mature protease. The mature protease may be combined with any propeptide, i.e., the mature protease may be combined with its native propeptide or a variant thereof, or with any other propeptide that is contemplated to have a beneficial effect on expression of said mature protease.

The mature protease may be a serine protease, cysteine protease, threonine protease, aspartic protease, glutamic protease, metalloprotease, or an asparagine peptide lyase. Similarly, the propeptide may be a serine protease propeptide, cysteine protease propeptide, threonine protease propeptide, aspartic protease propeptide, glutamic protease propeptide, metalloprotease propeptide, or an asparagine peptide lyase propeptide.

Serine proteases may be further divided into different groups according to substrate specificity (https://en.wikipedia.org/wiki/Serine_protease). Thus, in a preferred embodiment, the mature protease is selected from the group consisting of trypsin-like protease, chymotrypsin-like protease, thrombin-like protease, elastase-like protease, and subtilisin-like protease. Similarly, the propeptide may be selected from the group consisting of trypsin-like protease propeptide, chymotrypsin-like protease propeptide, thrombin-like protease propeptide, elastase-like protease propeptide, and subtilisin-like protease propeptide.

Serine protease may be even further divided into superfamilies, which again may be divided into several families (Rawlings et al., MEROPS: the database of proteolytic enzymes, their substrates and inhibitors, *Nucleic Acid Research,* 2012, vol. 40, D343-50). Thus, in a preferred embodiment, the mature protease is an S8 protease; preferably the mature protease is an S8A protease. Similarly, the propeptide may be an S8 protease propeptide; preferably the propeptide is an S8A propeptide. In a preferred embodiment, the mature protease is an S8A protease and the propeptide is a S8A protease propeptide.

The mature protease may be a native or an exogenous protease. The protease may comprise a C- or N-terminal propeptide and/or an N-terminal signal peptide.

Preferably, the mature protease of the invention has a sequence identity to the mature polypeptide of SEQ ID NO:2 of at least 80%, e.g., at least 85%, at least 90%, at least 91%, at least 92%, at least 93%, at least 94%, at least 95%, at least 96%, at least 97%, at least 98%, at least 99%, or 100%. Such mature protease may differ by up to 10 amino acids, e.g., 1, 2, 3, 4, 5, 6, 7, 8, 9, or 10, from the mature polypeptide of SEQ ID NO:2. Also preferably, the mature protease of the invention has a sequence identity to the mature polypeptide of SEQ ID NO:6 of at least 80%, e.g., at least 85%, at least 90%, at least 91%, at least 92%, at least 93%, at least 94%, at least 95%, at least 96%, at least 97%, at least 98%, at least 99%, or 100%. Such protease may differ by up to 10 amino acids, e.g., 1, 2, 3, 4, 5, 6, 7, 8, 9, or 10, from the mature polypeptide of SEQ ID NO:6.

In a preferred embodiment, the mature protease has a sequence identity to the mature polypeptide of SEQ ID NO:2 or SEQ ID NO:6 of at least 80%, e.g., at least 85%, at least 90%, at least 91%, at least 92%, at least 93%, at least 94%, at least 95%, at least 96%, at least 97%, at least 98%, at least 99%, or 100%.

Likewise, and preferably, the propeptide of the invention has a sequence identity to the polypeptide of SEQ ID NO:4 of at least 80%, e.g., at least 85%, at least 90%, at least 91%, at least 92%, at least 93%, at least 94%, at least 95%, at least 96%, at least 97%, at least 98%, at least 99%, or 100%. Such propeptide may differ by up to 10 amino acids, e.g., 1, 2, 3, 4, 5, 6, 7, 8, 9, or 10, from the polypeptide of SEQ ID NO:4. Also preferably, the propeptide of the invention has a sequence identity to the polypeptide of SEQ ID NO:8 of at least 80%, e.g., at least 85%, at least 90%, at least 91%, at least 92%, at least 93%, at least 94%, at least 95%, at least 96%, at least 97%, at least 98%, at least 99%, or 100%. Such propeptide may differ by up to 10 amino acids, e.g., 1, 2, 3, 4, 5, 6, 7, 8, 9, or 10, from the polypeptide of SEQ ID NO:8.

In a preferred embodiment, the propeptide has a sequence identity to the polypeptide of SEQ ID NO:4 or SEQ ID NO:8 of at least 80%, e.g., at least 85%, at least 90%, at least 91%, at least 92%, at least 93%, at least 94%, at least 95%, at least 96%, at least 97%, at least 98%, at least 99%, or 100%.

In an embodiment, the present invention relates to isolated mature proteases having a sequence identity to the mature polypeptide of SEQ ID NO:2 of at least 80%, e.g., at least 85%, at least 90%, at least 91%, at least 92%, at least 93%, at least 94%, at least 95%, at least 96%, at least 97%, at least 98%, at least 99%, or 100%, which have protease activity. In one aspect, the isolated protease differ by up to 10 amino acids, e.g., 1, 2, 3, 4, 5, 6, 7, 8, 9, or 10, from the mature polypeptide of SEQ ID NO:2. Also in an embodiment, the present invention relates to isolated mature proteases having a sequence identity to the mature polypeptide of SEQ ID NO:6 of at least 80%, e.g., at least 85%, at least 90%, at least 91%, at least 92%, at least 93%, at least 94%, at least 95%, at least 96%, at least 97%, at least 98%, at least 99%, or 100%, which have protease activity. In one aspect, the isolated protease differ by up to 10 amino acids, e.g., 1, 2, 3, 4, 5, 6, 7, 8, 9, or 10, from the mature polypeptide of SEQ ID NO:6.

Likewise, and in an embodiment, the present invention relates to isolated propeptides having a sequence identity to the polypeptide of SEQ ID NO:4 of at least 80%, e.g., at least 85%, at least 90%, at least 91%, at least 92%, at least 93%, at least 94%, at least 95%, at least 96%, at least 97%, at least 98%, at least 99%, or 100%. In one aspect, the isolated propeptides differ by up to 10 amino acids, e.g., 1, 2, 3, 4, 5, 6, 7, 8, 9, or 10, from the polypeptide of SEQ ID NO:4. Also in an embodiment, the present invention relates to isolated propeptides having a sequence identity to the polypeptide of SEQ ID NO:8 of at least 80%, e.g., at least 85%, at least 90%, at least 91%, at least 92%, at least 93%, at least 94%, at least 95%, at least 96%, at least 97%, at least 98%, at least 99%, or 100%. In one aspect, the isolated propeptides differ by up to 10 amino acids, e.g., 1, 2, 3, 4, 5, 6, 7, 8, 9, or 10, from the polypeptide of SEQ ID NO:8.

A mature protease of the present invention preferably comprises or consists of the mature polypeptide coding sequence of SEQ ID NO:2 or SEQ ID NO:6 or allelic variants thereof; or is a fragment thereof having protease activity.

A propeptide of the present invention preferably comprises or consists of the amino acid sequence of SEQ ID NO:4 or SEQ ID NO:8 or allelic variants thereof; or is a fragment thereof having propeptide activity.

In another embodiment, the present invention relates to an isolated polypeptide having protease activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO:1 or SEQ ID NO:5, or (ii) the full-length complement of (i) (Sambrook et al., 1989, *Molecular Cloning, A Laboratory Manual,* 2d edition, Cold Spring Harbor, N.Y.).

In another embodiment, the present invention relates to an isolated polypeptide having propeptide activity encoded by a polynucleotide that hybridizes under very low stringency conditions, low stringency conditions, medium stringency conditions, medium-high stringency conditions, high stringency conditions, or very high stringency conditions with (i) the polypeptide coding sequence of SEQ ID NO:3 SEQ ID NO:7, or (ii) the full-length complement of (i) (Sambrook et al., 1989, supra)

The polynucleotide of SEQ ID NO:1 or SEQ ID NO:5, or subsequences thereof, as well as the polypeptide of SEQ ID NO:2 or SEQ ID NO:6, or fragments thereof, may be used to design nucleic acid probes to identify and clone DNA encoding polypeptides having protease activity from strains of different genera or species according to methods well-known in the art.

Similarly, the polynucleotide of SEQ ID NO:3 or SEQ ID NO:7, or subsequences thereof, as well as the polypeptide of SEQ ID NO:4 or SEQ ID NO:8, or a fragments thereof, may be used to design nucleic acid probes to identify and clone DNA encoding polypeptides having propeptide activity.

In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having protease or propeptide activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO:1 or SEQ ID NO:5 (for mature proteases) or subsequences thereof, or with SEQ ID NO:3 or SEQ ID NO:7 (for propeptides) or subsequences thereof, the carrier material is used in a Southern blot.

For purposes of the mature proteases of present invention, hybridization indicates that the polynucleotide hybridizes to a labeled nucleic acid probe corresponding to (i) SEQ ID NO:1 or SEQ ID NO:5; (ii) the mature polypeptide coding sequence of SEQ ID NO:1 or SEQ ID NO:5; (iii) the full-length complements thereof; or (iv) subsequences thereof; under very low to very high stringency conditions. Molecules to which the nucleic acid probe hybridizes under these conditions can be detected using, for example, X-ray film or any other detection means known in the art.

For purposes of the propeptides of present invention, hybridization indicates that the polynucleotide hybridizes to a labeled nucleic acid probe corresponding to (i) SEQ ID NO:3 or SEQ ID NO:7; (ii) the full-length complements thereof; or (iii) subsequences thereof; under very low to very high stringency conditions. Molecules to which the nucleic acid probe hybridizes under these conditions can be detected using, for example, X-ray film or any other detection means known in the art.

In another embodiment, the present invention relates to an isolated polypeptide having protease activity encoded by a polynucleotide having a sequence identity to the mature polypeptide coding sequence of SEQ ID NO:1 or SEQ ID NO:5 of at least 80%, e.g., at least 85%, at least 90%, at least 91%, at least 92%, at least 93%, at least 94%, at least 95%, at least 96%, at least 97%, at least 98%, at least 99%, or 100%.

In another embodiment, the present invention relates to an isolated polypeptide having propeptide activity encoded by a polynucleotide having a sequence identity to the polypeptide coding sequence of SEQ ID NO:3 or SEQ ID NO:7 of at least 80%, e.g., at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO:2 or SEQ ID NO:6 comprising a substitution, deletion, and/or insertion at one or more (e.g., several) positions. In an embodiment, the number of amino acid substitutions, deletions and/or insertions introduced into the mature polypeptide of SEQ ID NO:2 or SEQ ID NO:6 is up to 10, e.g., 1, 2, 3, 4, 5, 6, 7, 8, 9, or 10.

In another embodiment, the present invention relates to variants of the polypeptide of SEQ ID NO:4 or SEQ ID NO:8 comprising a substitution, deletion, and/or insertion at one or more (e.g., several) positions. In an embodiment, the number of amino acid substitutions, deletions and/or insertions introduced into the polypeptide of SEQ ID NO:4 or SEQ ID NO:8 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the polypeptide; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptide are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease or propeptide activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The mature protease may be a hybrid protease in which a region of one mature protease is fused at the N-terminus or the C-terminus of a region of another mature protease.

Similarly, the propeptide may be a hybrid propeptide in which a region of one propeptide is fused at the N-terminus or the C-terminus of a region of another propeptide.

The mature proteases and/or propeptides may be a fusion polypeptides or cleavable fusion polypeptides in which another polypeptide is fused at the N-terminus or the C-terminus of the protease/propeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

Sources of Proteases and Propeptides

The mature proteases and propeptides of the present invention may, independently, be obtained from microorganisms of any genus. For purposes of the present invention, the term "obtained from" as used herein in connection with a given source shall mean that the mature protease and/or propeptide encoded by a polynucleotide is produced by the source or by a strain in which the polynucleotide from the source has been inserted. In one aspect, the mature protease and/or propeptide obtained from a given source is secreted extracellularly.

The mature protease and/or propeptide may be an archeal mature protease and/or propeptide. In a preferred embodiment, the protease and/or propeptide are obtained from a *Pyrrococcus* species. More preferably, the mature protease and/or propeptide are obtained from *Pyrrococcus furiosus*. Even more preferably, the mature protease is the mature PfuS or a variant thereof, and the propeptide is the PfuS propeptide or a variant thereof.

The mature protease and/or propeptide may also be a bacterial protease and/or propeptide. For example, the protease and/or propeptide may, independently, be obtained from a Gram-positive bacteria such as a *Bacillus, Clostridium, Enterococcus, Geobacillus, Lactobacillus, Lactococcus, Oceanobacillus, Staphylococcus, Streptococcus*, or *Streptomyces* species, or a Gram-negative bacteria such as a *Campylobacter, E. coli, Flavobacterium, Fusobacterium, Helicobacter, Ilyobacter, Neisseria, Pseudomonas, Salmonella*, or *Ureaplasma* species.

In a preferred embodiment, the mature protease and/or propeptide are, independently, obtained from *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, or *Bacillus thuringiensis*.

In a preferred embodiment, the protease and/or propeptide are obtained from a *Bacillus* species. More preferably, the mature protease and/or propeptide are obtained from *Bacillus horneckiae*. Even more preferably, the mature protease is the mature BH-S8A or a variant thereof, and the propeptide is the BH-S8A propeptide or a variant thereof.

In a preferred embodiment, the mature protease and/or propeptide are, independently, obtained from *Streptococcus equisimilis, Streptococcus pyogenes, Streptococcus uberis*, or *Streptococcus equi* subsp. *Zooepidemicus*.

In a preferred embodiment, the mature protease and/or propeptide are, independently, obtained from *Streptomyces achromogenes, Streptomyces avermitilis, Streptomyces coelicolor, Streptomyces griseus*, or *Streptomyces lividans*.

The mature protease and/or propeptide also may be a fungal mature protease and propeptide. For example, the mature protease and/or propeptide may be a yeast mature protease and/or propeptide such as a *Candida, Kluyveromyces, Pichia, Saccharomyces, Schizosaccharomyces*, or *Yarrowia* mature protease and/or propeptide; or a filamentous fungal mature protease and/or propeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* mature protease and/or propeptide.

In another embodiment, the mature protease and/or propeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* mature protease and/or propeptide.

In another embodiment, the mature protease and/or propeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* mature protease and/or propeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The mature protease and the propeptide of the present invention may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. Polynucleotides encoding the protease and/or propeptide may then be obtained by similarly screening a genomic DNA or cDNA library of another microorganism or mixed DNA sample. Once polynucleotides encoding a mature protease and/or propeptide have been detected with the probe(s), the polynucleotides can be isolated or cloned by utilizing techniques that are known to those of ordinary skill in the art (see, e.g., Sambrook et al., 1989, supra).

Methods of Production

In a second aspect, the present invention relates to methods for producing a mature protease of the invention, said method comprising the steps of:

a) providing a prokaryotic host cell comprising in its genome at least one polynucleotide encoding a protease proenzyme comprising a mature protease and at least one polynucleotide encoding a propeptide of said mature protease, wherein the polynucleotide encoding the protease proenzyme and the polynucleotide encoding the propeptide of said protease are not expressed as a translationally fused protein;
b) cultivating said prokaryotic host cell under conditions conducive for expression of the mature protease; and, optionally,
c) recovering the mature protease.

In a preferred embodiment, the mature protease has a sequence identity to the mature polypeptide of SEQ ID NO:2 or SEQ ID NO:6 of at least 80%, e.g., at least 85%, at least 90%, at least 91%, at least 92%, at least 93%, at least 94%, at least 95%, at least 96%, at least 97%, at least 98%, at least 99%, or 100%.

Also in a preferred embodiment, the propeptide has a sequence identity to the polypeptide of SEQ ID NO:4 or SEQ ID NO:8 of at least 80%, e.g., at least 85%, at least 90%, at least 91%, at least 92%, at least 93%, at least 94%, at least 95%, at least 96%, at least 97%, at least 98%, at least 99%, or 100%.

In a preferred embodiment, the mature protease comprises or consists of the mature polypeptide coding sequence of SEQ ID NO:2 or SEQ ID NO:6 or allelic variants thereof; or is a fragment thereof having protease activity.

Also in a preferred embodiment, the propeptide comprises or consists of the amino acid sequence of SEQ ID NO:4 or SEQ ID NO:8 or allelic variants thereof; or is a fragment thereof having propeptide activity.

In a preferred embodiment, the mature protease is PfuS or BH-S8A, and the propeptide is PfuS propeptide or BH-S8A propeptide.

The prokaryotic host cells are cultivated in a nutrient medium suitable for production of the mature protease using methods known in the art. For example, the prokaryotic host cells may be cultivated by shake flask cultivation, or small-scale or large-scale fermentation (including continuous, batch, fed-batch, or solid state fermentations) in laboratory or industrial fermentors in a suitable medium and under conditions allowing the mature protease to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the mature protease is secreted into the nutrient medium, it can be recovered directly from the medium. If the mature protease is not secreted, it can be recovered from cell lysates.

The mature protease may be recovered using methods known in the art. For example, the mature protease may be recovered from the nutrient medium by conventional procedures including, but not limited to, collection, centrifugation, filtration, extraction, spray-drying, evaporation, or precipitation. In one aspect, a fermentation broth comprising the mature protease is recovered.

In a preferred embodiment, the present invention relates to methods for producing PfuS, said method comprising the steps of:

a) providing a prokaryotic host cell comprising in its genome at least one polynucleotide encoding PfuS proenzyme comprising mature PfuS and at least one polynucleotide encoding the PfuS propeptide or a variant thereof, wherein the polynucleotide encoding PfuS proenzyme and the polynucleotide encoding the PfuS propeptide or a variant thereof are not expressed as a translationally fused protein;
b) cultivating said prokaryotic host cell under conditions conducive for expression of mature PfuS; and, optionally,
c) recovering mature PfuS.

Also in a preferred embodiment, the present invention relates to methods for producing BH-S8A, said method comprising the steps of:

a) providing a prokaryotic host cell comprising in its genome at least one polynucleotide encoding BH-S8A proenzyme comprising mature BH-S8A and at least one polynucleotide encoding the BH-S8A propeptide or a variant thereof, wherein the polynucleotide encoding BH-S8A proenzyme and the polynucleotide encoding the BH-S8A propeptide or a variant thereof are not expressed as a translationally fused protein;
b) cultivating said prokaryotic host cell under conditions conducive for expression of mature BH-S8A; and, optionally,
c) recovering mature BH-S8A.

However, it is likely that co-expression of a protease proenzyme comprising a mature protease and a propeptide of said mature protease may also be useful for improving the expression of other matures proteases than PfuS and BH-S8A. Such embodiments are also encompassed by the present invention.

In an alternative aspect, the mature protease is not recovered, but rather a prokaryotic host cell of the present invention expressing the protease proenzyme comprising the mature protease is used as a source of the mature protease.

Fermentation Broth Formulations or Cell Compositions

In a third aspect, the present invention relates to a fermentation broth formulation or a cell composition comprising a mature protease of the present invention. The fermentation broth product further comprises additional ingredients used in the fermentation process, such as, for example, cells (including, the prokaryotic host cells containing the polynucleotides encoding the protease proenzyme and the propeptide of the present invention which are used to produce the mature protease of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 1990/15861 or WO 2010/096673.

Enzyme Compositions

In a fourth aspect, the present invention relates to compositions comprising a mature protease and propeptide of the present invention.

The compositions may comprise a mature protease of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase; more preferably the enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

The present invention is further described by the following examples that should not be construed as limiting the scope of the invention.

EXAMPLES

Materials and Methods

Media:

*Bacillus* strains were grown on LB agar (10 g/l Tryptone, 5 g/l yeast extract, 5 g/l NaCl, 15 g/l agar) plates, on Difco Tryptose Blood Agar Base plates, or in LB liquid medium (10 g/l Tryptone, 5 g/l yeast extract, 5 g/l NaCl).

To select for erythromycin resistance, agar media were supplemented with 1 μg/ml erythromycin and 25 μg/ml lincomycin, and liquid media were supplemented with 5 μg/ml erythromycin.

Spizizen I and Spizizen II media were used for preparation and transformation of competent *Bacillus subtilis* cells.

Spizizen I medium consists of 1× Spizizen salts (6 g/l KH2PO4, 14 g/l K2HPO4, 2 g/l (NH4)2SO4, 1 g/l sodium citrate dihydrate, 0.2 g/l MgSO4.7H20, pH 7.0), 0.5% glucose, 0.1% yeast extract, and 0.02% casein hydrolysate.

Spizizen II medium consists of Spizizen I medium supplemented with 0.5 mM CaCl2), and 2.5 mM MgCl2.

Conjugation donor strains were supplemented with 100 μg/ml D-alanine.

Strains:

*Bacillus subtilis* PP3724 and *Bacillus subtilis* BW390. These strains are donor strains for conjugation of *Bacillus* strains as described in WO 1996/029418.

*Bacillus licheniformis* SJ1904: This strain is described in WO 2008/066931.

Molecular Biology Methods:

Competent cells of *Bacillus subtilis* strains prepared and transformed according to the method described in Yasbin et al. (1973): Transformation and transfection in lysogenic strains of *Bacillus subtilis* 168. *J. Bacteriol.* 113, 540-548.

Conjugation of *Bacillus licheniformis* was performed essentially as described in WO 1996/029418.

Protease Assay:

Samples of whole culture broth were diluted in sample buffer (0.01% Triton, 50 mM Tris.HCl, 1 mM $CaC_2$, 150 mM NaCl, pH 8.5). For PfuS, samples were diluted 10-fold in sample buffer, followed by a heat pretreatment of 2 h at 65° C. to lyse cells and activate the protease; samples were then further diluted 200-fold in sample buffer. For BH-S8A, samples were diluted 40,000-fold in sample buffer. Throughout the assay the temperature was maintained at 37° C. A succinyl-Ala-Ala-Pro-Phe-p-nitroanilide substrate solution was prepared by diluting a 100 mg/mL stock solution (in DMSO) 1:55.6 in sample buffer. 160 μl of substrate solution was added to each sample cuvette and incubated for 480 s to equilibrate the temperature. 40 μl of diluted culture broth sample was then added to a corresponding cuvette and incubated for an additional 60 s. Following this incubation step, the absorbance of the samples was monitored at 405 nm for 190 s, and rate of change of absorbance was calculated for all samples. Sample concentrations were determined by comparison with a standard curve generated using a PfuS standard of known activity, diluted appropriately in sample buffer to seven values over a 5-fold range.

Example 1. Construction of *Bacillus licheniformis* Strain Expressing PfuS

Plasmid pMDT251 was constructed for insertion of a gene encoding PfuS (designated by gene name aprPfuS) into the genome of a *Bacillus* host using the site-specific recombinase-mediated method described in WO 2006/042548. A map of pMDT251 is shown in FIG. 1, the DNA sequence of the PfuS coding region is shown in SEQ ID NO:1, and the corresponding amino acid sequence is shown in SEQ ID NO:2. Plasmid pMDT251 comprises aprPfuS flanked upstream by the cryIIIA mRNA stabilizer region (WO 1994/025612) and downstream by the attP site of lactococcal bacteriophage TP901-1 (WO 2006/042548). Plasmid pMDT251 was introduced into conjugation donor strain *Bacillus subtilis* PP3724 by transformation, resulting in strain PP3724/pMDT251.

Using conjugation donor strain PP3724/pMDT251, plasmid pMDT251 was introduced by conjugation into a derivative of *Bacillus licheniformis* SJ1904 comprising five chromosomal target sites for insertion of the plasmid and deletions in the genes encoding alkaline protease (aprL) and Glu-specific protease (mprL). At each of the five chromosomal target sites of the *B. licheniformis* host is an expression cassette comprising a promoter followed by the cryIIIA mRNA stabilizer region, a marker gene (encoding either a fluorescent protein or an antibiotic resistance marker), and the attB site of lactococcal bacteriophage TP901-1. The plasmid inserted into the *B. licheniformis* chromosome by site-specific recombination between the attP site on the plasmid and attB sites at the target chromosomal loci. The plasmid was then allowed to excise from the chromosome via homologous recombination between the cryIIIA stabilizer regions on the plasmid and in the target chromosomal locus by incubation at 34° C. in the absence of erythromycin selection. Integrants that had lost the plasmid were selected by screening for erythromycin sensitivity and loss of marker phenotypes (fluorescence or antibiotic resistance). Integration of the aprPfuS gene was confirmed by PCR analysis. One *B. licheniformis* integrant with the aprPfuS gene inserted at three chromosomal loci was designated MDT424. MDT424 therefore has two remaining chromosomal target sites comprising marker genes.

Figure 2:
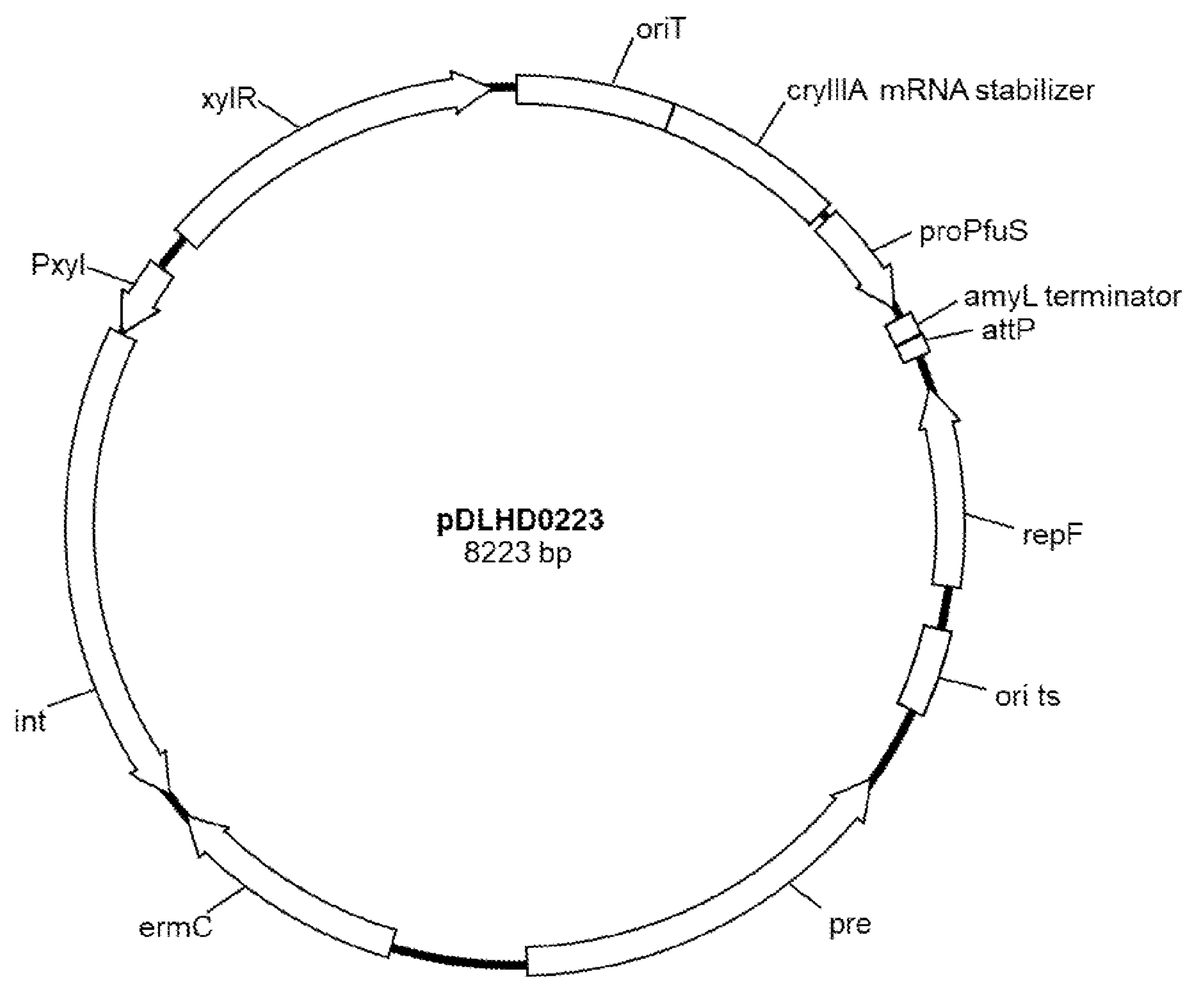
FIG. 2 shows a plasmid map of pDLHD0223, which comprises the proPfuS gene flanked upstream by the cryIIIA mRNA stabilizer region and downstream by the attP site of lactococcal bacteriophage TP901-1, and was introduced into conjugation donor strain *Bacillus subtilis* BW390 by transformation, resulting in strain BW390/pDLHD0223, as described in Example 2.

Example 2. Construction of *Bacillus licheniformis* Strains Co-Expressing PfuS and PfuS Propeptide Plasmid pDLHD0223 was constructed for insertion of a gene encoding the N-terminal propeptide of PfuS (designated by gene name proPfuS) into the genome of a *Bacillus* host using the site-specific recombinase-mediated method described in WO 2006/042548. A map of pDLHD0223 is shown in FIG. 2, the DNA sequence of the PfuS propeptide coding region is shown in SEQ ID NO:3, and the corresponding amino acid sequence is shown in SEQ ID NO:4. Plasmid pDLHD0223 comprises proPfuS flanked upstream by the cryIIIA mRNA stabilizer region and downstream by the attP site of lactococcal bacteriophage TP901-1. Plasmid pDLHD0223 was introduced into conjugation donor strain *Bacillus subtilis* BW390 by transformation, resulting in strain BW390/pDLHD0223.

Using conjugation donor strain BW390/pDLHD0223, plasmid pDLHD0223 was introduced by conjugation into *Bacillus licheniformis* MDT424. The plasmid inserted into the *B. licheniformis* chromosome by site-specific recombination between the attP site on the plasmid and attB sites at the target chromosomal loci. The plasmid was then allowed to excise from the chromosome via homologous recombination between the cryIIIA stabilizer regions on the plasmid and in the target chromosomal locus by incubation at 34° C. in the absence of erythromycin selection. Integrants that had lost the plasmid were selected by screening for erythromycin sensitivity and loss of marker phenotypes (fluorescence or antibiotic resistance). Integration of the proPfuS gene was confirmed by PCR analysis. One MDT424 integrant with the proPfuS gene inserted at one chromosomal locus was designated MaTa251. One MDT424 integrant with the proPfuS gene inserted at two chromosomal loci was designated MaTa254.

Example 3. Comparison of PfuS Production by *Bacillus licheniformis* Integrants Expressing PfuS and the PfuS Propeptide

Figure 3:
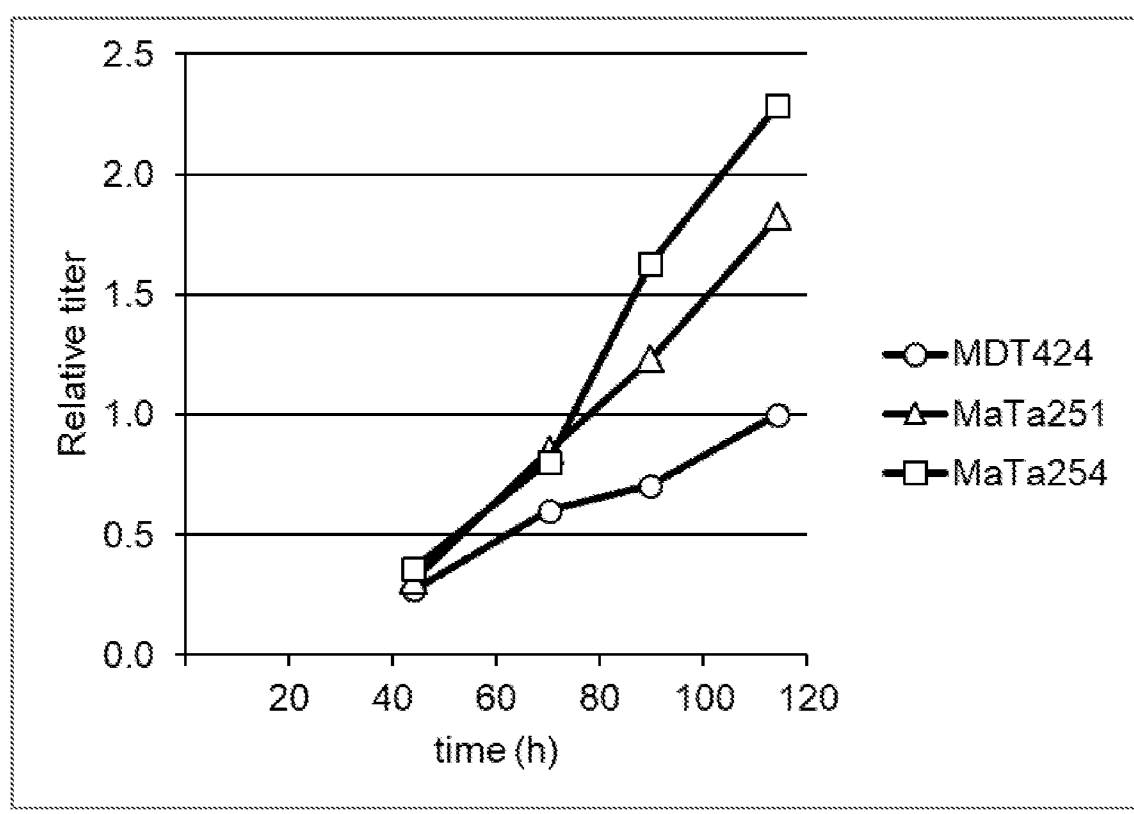
FIG. 3 shows relative PfuS titer for *B. licheniformis* strains co-expressing PfuS and PfuS propeptide, as described in Example 3. MDT424 is a *Bacillus licheniformis* strain used to introduce plasmid pDLH0223 that comprises the ProPfuS gene by conjugation with donor strain *Bacillus subtilis* BW390/pDLH0223 at one locus or two loci. MaTa251 is an MDT424 integrant with the proPfuS gene inserted at one chromosomal locus. MaTa254 is an MDT424 integrant with the proPfuS gene inserted at two chromosomal loci.
Figure 4:
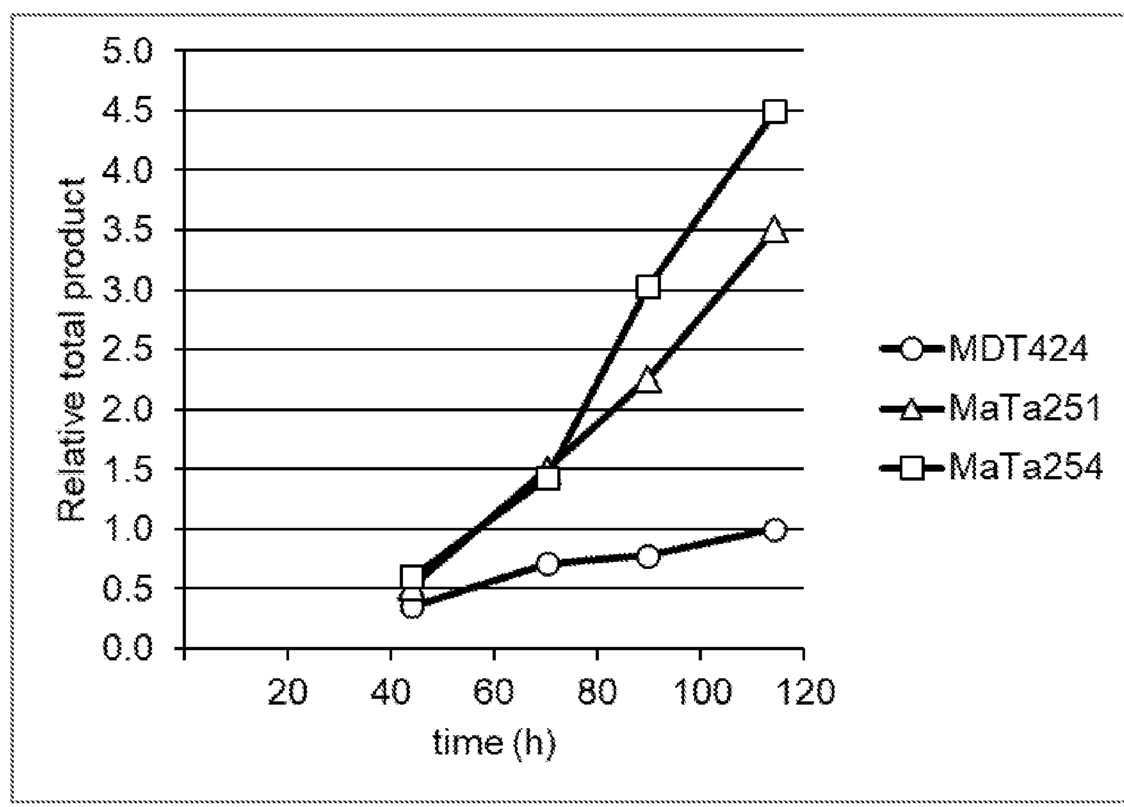
FIG. 4 shows relative total PfuS product for *B. licheniformis* strains co-expressing PfuS and the PfuS propeptide, as described in Example 3. MDT424 is a *Bacillus licheniformis* strain used to introduce plasmid pDLH0223 that comprises the ProPfuS gene by conjugation with donor strain *Bacillus subtilis* BW390/pDLH0223 at one locus or two loci. MaTa251 is an MDT424 integrant with the proPfuS gene inserted at one chromosomal locus. MaTa254 is an MDT424 integrant with the proPfuS gene inserted at two chromosomal loci.

*B. licheniformis* strains MDT424, MaTa251, and MaTa254 were cultivated, and PfuS production by the strains was compared using enzyme activity assay. Relative PfuS titer and total PfuS product are shown in Table 1 and FIGS. 3 and 4. PfuS titer increased relative to MDT424 with each additional copy of the propeptide gene. Fermentation broths of strains MaTa251 and MaTa254 became less viscous than that of MDT424, which was associated with higher dissolved oxygen tension (DOT). Because the glucose feed was restricted when the DOT dropped below 20%, the MaTa251 and MDT254 cultivations received more glucose feed and therefore had higher final culture volumes. This resulted in greater total PfuS product beyond what can be accounted for by the increases in titer alone.

TABLE 1

Relative PfuS titer and total PfuS product for *B. licheniformis* strains co-expressing PfuS and its propeptide.

| Strain | Number of PfuS gene copies | Number of propeptide gene copies | Relative titer | Relative total product |
|---|---|---|---|---|
| MDT424 | 3 | 0 | 1.0 | 1.0 |
| MaTa251 | 3 | 1 | 1.8 | 3.5 |
| MaTa254 | 3 | 2 | 2.3 | 4.5 |

Example 4. Construction of *Bacillus licheniformis* Strain Expressing BH-S8A

Figure 5:
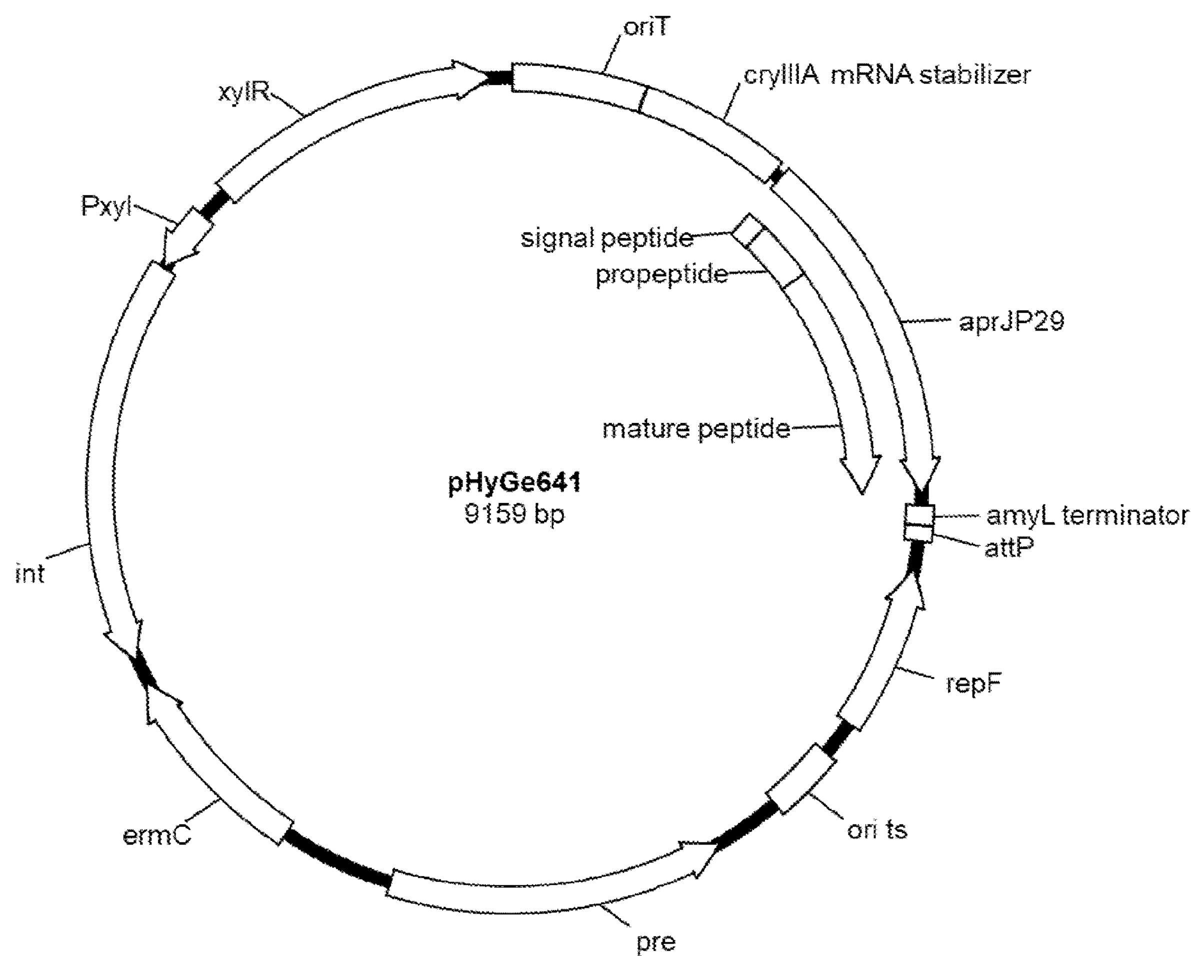
FIG. 5 shows a plasmid map of pHyGe641, which comprises the aprJP29 gene flanked upstream by the cryIIIA mRNA stabilizer region and downstream by the attP site of lactococcal bacteriophage TP901-1, and was introduced into conjugation donor strain *Bacillus subtilis* PP3724 by transformation, resulting in strain PP3724/pHyGe641, as described in Example 4.

Plasmid pHyGe641 was constructed for insertion of a gene encoding BH-S8A (designated by gene name aprJP29) into the genome of a *Bacillus* host using the site-specific recombinase-mediated method described in WO 2006/042548. A map of pHyGe641 is shown in FIG. 5, the DNA sequence of the BH-S8A coding region is shown in SEQ ID NO:5, and the corresponding amino acid sequence is shown in SEQ ID NO:6. Plasmid pHyGe641 comprises aprJP29 flanked upstream by the cryIIIA mRNA stabilizer region (WO 1994/025612) and downstream by the attP site of lactococcal bacteriophage TP901-1 (WO 2006/042548). Plasmid pHyGe641 was introduced into conjugation donor strain *Bacillus subtilis* PP3724 by transformation, resulting in strain PP3724/pHyGe641.

Using conjugation donor strain PP3724/pHyGe641, plasmid pHyGe641 was introduced by conjugation into the derivative of *B. licheniformis* SJ1904 described in Example 1. The plasmid inserted into the *B. licheniformis* chromosome by site-specific recombination between the attP site on the plasmid and attB sites at the target chromosomal loci. The plasmid was then allowed to excise from the chromosome via homologous recombination between the cryIIIA stabilizer regions on the plasmid and in the target chromosomal locus by incubation at 34° C. in the absence of erythromycin selection. Integrants that had lost the plasmid were selected by screening for erythromycin sensitivity and loss of marker phenotypes (fluorescence or antibiotic resistance). Integration of the aprJP29 gene was confirmed by PCR analysis. One *B. licheniformis* integrant with the aprJP29 gene inserted at three chromosomal loci was designated HyGe644. HyGe644 therefore has two remaining chromosomal target sites comprising marker genes.

Figure 6:
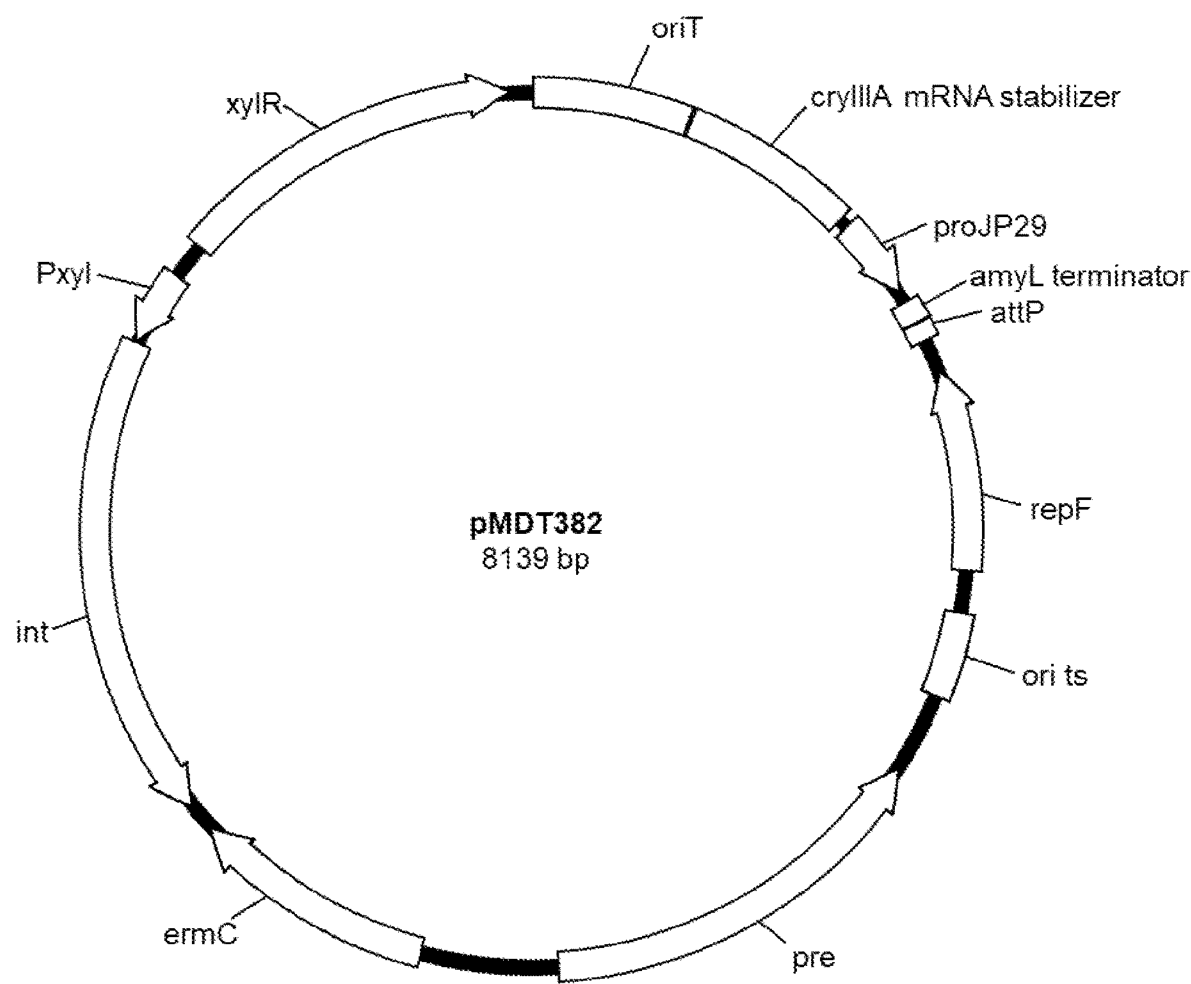
FIG. 6 shows a plasmid map of pMDT382, which comprises the proJP29 gene flanked upstream by the cryIIIA mRNA stabilizer region and downstream by the attP site of lactococcal bacteriophage TP901-1, and was introduced into conjugation donor strain *Bacillus subtilis* PP3724 by transformation, resulting in strain PP3724/pMDT382, as described in Example 5.

Example 5. Construction of *Bacillus licheniformis* Strains Co-Expressing BH-S8A and BH-S8A Propeptide Plasmid pMDT382 was constructed for insertion of a gene encoding the N-terminal propeptide of BH-S8A (designated by gene name proJP29) into the genome of a *Bacillus* host using the site-specific recombinase-mediated method described in WO 2006/042548. A map of pMDT382 is shown in FIG. 6, the DNA sequence of the BH-S8A propeptide coding region is shown in SEQ ID NO:7, and the corresponding amino acid sequence is shown in SEQ ID NO:8. Plasmid pMDT382 comprises proJP29 flanked upstream by the cryIIIA mRNA stabilizer region and downstream by the attP site of lactococcal bacteriophage TP901-1. Plasmid pMDT382 was introduced into conjugation donor strain *Bacillus subtilis* PP3724 by transformation, resulting in strain PP3724/pMDT382.

Using conjugation donor strain PP3724/pMDT382, plasmid pMDT382 was introduced by conjugation into *Bacillus licheniformis* HyGe644. The plasmid inserted into the *B. licheniformis* chromosome by site-specific recombination between the attP site on the plasmid and attB sites at the target chromosomal loci. The plasmid was then allowed to excise from the chromosome via homologous recombination between the cryIIIA stabilizer regions on the plasmid and in the target chromosomal locus by incubation at 34° C. in the absence of erythromycin selection. Integrants that had lost the plasmid were selected by screening for erythromycin sensitivity and loss of marker phenotypes (fluorescence or antibiotic resistance). Integration of the proJP29 gene was confirmed by PCR analysis. One HyGe644 integrant with the proJP29 gene inserted at one chromosomal locus was designated MDT664. One HyGe644 integrant with the proJP29 gene inserted at two chromosomal loci was designated MDT665.

Example 6. Comparison of BH-S8A Production by *Bacillus licheniformis* Integrants Expressing BH-S8A and the BH-S8A Propeptide

Figure 7:
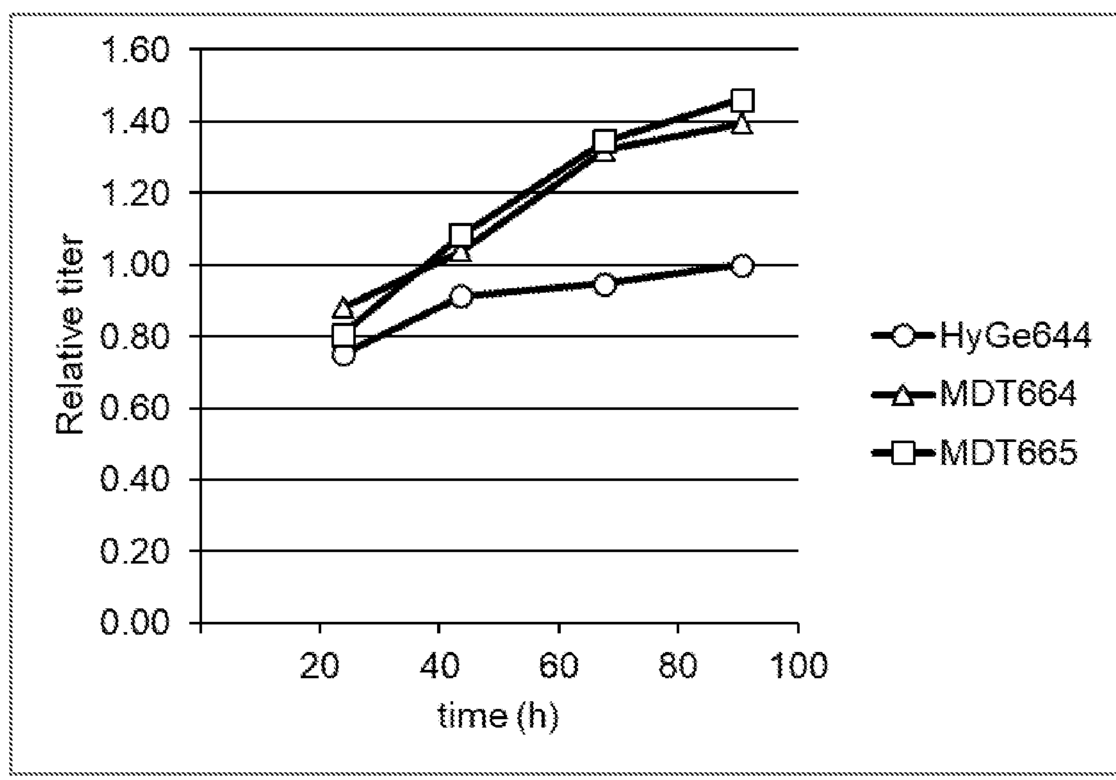
FIG. 7 shows relative BH-S8A titer for *B. licheniformis* strains co-expressing BH-S8A and BH-S8A propeptide, as described in Example 6. HyGe644 is a *Bacillus licheniformis* strain used to introduce plasmid pMDT382 that comprises the proJP29 gene by conjugation with donor strain *Bacillus subtilis* PP3724 by transformation, resulting in PP3724/pMDT382 at one locus or two loci. MDT664 is an HyGe644 integrant with the proJP29 gene inserted at one chromosomal locus. MDT665 is an HyGe644 integrant with the proJP29 gene inserted at two chromosomal loci.

*B. licheniformis* strains HyGe644, MDT664, and MDT665 were cultivated, and BH-S8A production by the strains was compared using enzyme activity assay. Relative BH-S8A titers are shown in Table 2 and FIG. 7. BH-S8A titer increased relative to HyGe644 with each additional copy of the propeptide gene.

TABLE 2

Relative BH-S8A titer for *B. licheniformis* strains co-expressing BH-S8A and its pro-peptide.

| Strain | Number of Protease S8A gene copies | Number of propeptide gene copies | Relative titer |
|---|---|---|---|
| HyGe644 | 3 | 0 | 1.0 |
| MDT664 | 3 | 1 | 1.4 |
| MDT665 | 3 | 2 | 1.5 |

The invention claimed is:

1. A recombinant *Bacillus* host cell comprising in its genome at least one polynucleotide encoding a protease proenzyme, where the host cell further comprises at least one polynucleotide encoding the propeptide alone, wherein the at least one polynucleotide encoding the protease proenzyme and the at least one polynucleotide encoding the propeptide are not expressed as a translationally fused protein, wherein the mature protease has an amino acid sequence that has at least 90% sequence identity to the mature polypeptide of SEQ ID NO: 2; or wherein the mature protease has an amino acid sequence that has at least 90% sequence identity to the mature polypeptide of SEQ ID NO: 6;

and wherein the propeptide has an amino acid sequence that has at least 90% sequence identity to SEQ ID NO: 4; or wherein the propeptide has an amino acid sequence that has at least 90% sequence identity to SEQ ID NO: 8.

2. The *Bacillus* host cell according to claim 1, which is selected from the group consisting of *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis* cells.

3. The *Bacillus* host cell according to claim 1, wherein the polynucleotide encoding the protease proenzyme comprises a polynucleotide encoding the mature protease that has at least 90% sequence identity to SEQ ID NO: 1; OR wherein the polynucleotide encoding the protease proenzyme comprises a polynucleotide encoding the mature protease that has at least 90% sequence identity to SEQ ID NO: 5.

4. The *Bacillus* host cell according to claim 1, wherein the polynucleotide encoding the propeptide has at least 90% sequence identity to SEQ ID NO: 3; OR wherein the polynucleotide encoding the propeptide has at least 90% sequence identity to SEQ ID NO: 7.

5. The *Bacillus* host cell according to claim 1, wherein the mature protease comprises or consists of *Pyrococcus furiosus* Protease S (PfuS); OR wherein the mature protease comprises or consists of *Bacillus horneckiae* Protease S8A (BH-S8A).

6. The *Bacillus* host cell according to claim 1, wherein the propeptide comprises or consists of the *Pyrococcus furiosus* Protease S (PfuS) propeptide; OR wherein the propeptide comprises or consists of the *Bacillus* horneckiae Protease S8A (BH-S8A) propeptide.

7. The *Bacillus* host cell according to claim 1, wherein the at least one polynucleotide encoding the protease proenzyme and the at least one polynucleotide encoding the propeptide have been integrated into same locus or different loci in the genome of the prokaryotic host cell.

8. The *Bacillus* host cell according to claim 1, wherein the at least one polynucleotide encoding the protease proenzyme and the at least one polynucleotide encoding the propeptide are operably linked with a promotor in an operon.

9. The *Bacillus* host cell according to claim 1, wherein the at least one polynucleotide encoding the protease proenzyme and the at least one polynucleotide encoding the propeptide are each operably linked with a separate promoter.

10. A method for producing a mature protease having an amino acid sequence that has at least 90% sequence identity to the mature polypeptide of SEQ ID NO: 2 or SEQ ID NO: 6, the method comprising:

a. providing a *Bacillus* host cell according to claim 1;

b. cultivating said *Bacillus* host cell under conditions conducive for expression of the mature protease; and, optionally, c. recovering the mature protease.

11. The *Bacillus* host cell according to claim 1, which is a *Bacillus licheniformis* host cell.

12. The *Bacillus* host cell according to claim 9, wherein the separate promoters are identical copies of the same promoter.

13. The *Bacillus* host cell according to claim 1, wherein the mature protease has an amino acid sequence that has at least 95% sequence identity to the mature polypeptide of SEQ ID NO: 2; or wherein the mature protease has an amino acid sequence that has at least 95% sequence identity to the mature polypeptide of SEQ ID NO: 6.

14. The *Bacillus* host cell according to claim 1, wherein the mature protease has an amino acid sequence that has at least 97% sequence identity to the mature polypeptide of SEQ ID NO: 2; or wherein the mature protease has an amino acid sequence that has at least 97% sequence identity to the mature polypeptide of SEQ ID NO: 6.

15. The *Bacillus* host cell according to claim 1, wherein the polynucleotide encoding the protease proenzyme comprises a polynucleotide encoding the mature protease that has at least 95% sequence identity to SEQ ID NO: 1; OR wherein the polynucleotide encoding the protease proenzyme comprises a polynucleotide encoding the mature protease that has at least 95% sequence identity to SEQ ID NO: 5.

16. The *Bacillus* host cell according to claim 1, wherein the polynucleotide encoding the protease proenzyme comprises a polynucleotide encoding the mature protease that has at least 97% sequence identity to SEQ ID NO: 1; OR wherein the polynucleotide encoding the protease proenzyme comprises a polynucleotide encoding the mature protease that has at least 97% sequence identity to SEQ ID NO: 5.

17. The *Bacillus* host cell according to claim 1, wherein the propeptide has an amino acid sequence that has at least 95% sequence identity to SEQ ID NO: 4; or wherein the propeptide has an amino acid sequence that has at least 95% sequence identity to SEQ ID NO: 8.

18. The *Bacillus* host cell according to claim 1, wherein the propeptide has an amino acid sequence that has at least 97% sequence identity to SEQ ID NO: 4; or wherein the propeptide has an amino acid sequence that has at least 97% sequence identity to SEQ ID NO: 8.

19. The *Bacillus* host cell according to claim 1, wherein the polynucleotide encoding the propeptide has at least 95% sequence identity to SEQ ID NO: 3; OR wherein the polynucleotide encoding the propeptide has at least 95% sequence identity to SEQ ID NO: 7.

20. The *Bacillus* host cell according to claim 1, wherein the polynucleotide encoding the propeptide has at least 97% sequence identity to SEQ ID NO: 3; OR wherein the polynucleotide encoding the propeptide has at least 97% sequence identity to SEQ ID NO: 7.

* * * * *

SEQUENCE LISTING

```
<160> NUMBER OF SEQ ID NOS: 8

<210> SEQ ID NO 1
<211> LENGTH: 1572
<212> TYPE: DNA
<213> ORGANISM: Pyrococcus furiosus

<400> SEQUENCE: 1

atggcacctg agaagaaagt tgagcaagtt cgcaacgtag agaaaaacta cggtcttctt      60
```

```
acaccaggcc ttttccgcaa aatccaaaaa cttaacccta acgaggagat cagcactgta     120

atcgtttttg agaaccatcg cgagaaggag atcgctgttc gcgttcttga gcttatgggt     180

gcgaaggtac gctacgttta ccatatcatt ccggctattg cggctgacct taaggttcgc     240

gaccttcttg ttatctctgg tcttactggt ggcaaagcga aactttcagg cgttcgcttc     300

atccaagagg actacaaagt tactgtatct gctgagcttg agggacttga cgagtcagcg     360

gcacaagtaa tggcaacata cgtatggaac cttggctacg acggttctgg catcactatc     420

ggcatcatcg acacgggcat cgacgcttca caccctgacc ttcaaggtaa ggtaatcggt     480

tgggttgact tcgttaatgg tcgctcttat ccgtatgacg accatggcca cggtacacac     540

gtagcatcta tcgcagctgg cactggcgca gcttctaacg gcaagtacaa aggcatggca     600

cctggtgcga aacttgctgg tatcaaagta cttggcgcag acggctctgg ctcaatcagc     660

acaatcatca aaggcgttga gtgggctgtt gacaacaagg acaaatacgg tatcaaagtt     720

atcaaccttt ctcttggctc ttctcaaagc tctgacggca cagacgcgct ttcacaagct     780

gttaacgctg cttgggacgc tggtcttgta gttgttgttg ctgctggtaa cagcggtcca     840

aacaaataca ctatcggctc accggcagct gcgtctaaag taatcacagt tggagctgta     900

gacaaatacg acgttatcac ttctttctca tctcgtggcc ctactgcaga tggtcgcctt     960

aaaccagagg ttgtagcacc aggcaactgg atcatcgcag ctcgcgcttc tggcacatca    1020

atgggccaac caatcaacga ctactatact gctgcgccag gaacttctat ggctactcca    1080

cacgtagcag gtatcgctgc acttcttctt caagctcacc cttcttggac gcctgacaaa    1140

gtaaagactg cacttatcga gactgctgac atcgttaaac ctgacgagat cgcagacatc    1200

gcttatggtg ctggtcgcgt taatgcgtac aaggctatca actatgacaa ctatgctaaa    1260

cttgtattca cgggctacgt agctaacaaa ggctctcaaa cgcaccaatt tgttatctct    1320

ggcgcaagct tcgttactgc tactctttac tgggacaacg ctaactctga ccttgacctt    1380

tacttatacg acccaaacgg caaccaggtt gactattctt atactgcata ctacgacttt    1440

gagaaggttg gctattacaa ccctactgac ggcacatgga caatcaaagt agtaagctat    1500

tcaggatcag ctaactacca agtagacgta gtttctgacg gttctcttag ccagcctggc    1560

tcatcaccat aa                                                        1572
```

<210> SEQ ID NO 2
<211> LENGTH: 523
<212> TYPE: PRT
<213> ORGANISM: Pyrococcus furiosus

<400> SEQUENCE: 2

```
Met Ala Pro Glu Lys Lys Val Glu Gln Val Arg Asn Val Glu Lys Asn
1               5                   10                  15

Tyr Gly Leu Leu Thr Pro Gly Leu Phe Arg Lys Ile Gln Lys Leu Asn
            20                  25                  30

Pro Asn Glu Glu Ile Ser Thr Val Ile Val Phe Glu Asn His Arg Glu
        35                  40                  45

Lys Glu Ile Ala Val Arg Val Leu Glu Leu Met Gly Ala Lys Val Arg
    50                  55                  60

Tyr Val Tyr His Ile Ile Pro Ala Ile Ala Ala Asp Leu Lys Val Arg
65                  70                  75                  80

Asp Leu Leu Val Ile Ser Gly Leu Thr Gly Gly Lys Ala Lys Leu Ser
                85                  90                  95
```

```
Gly Val Arg Phe Ile Gln Glu Asp Tyr Lys Val Thr Val Ser Ala Glu
            100                 105                 110

Leu Glu Gly Leu Asp Glu Ser Ala Ala Gln Val Met Ala Thr Tyr Val
        115                 120                 125

Trp Asn Leu Gly Tyr Asp Gly Ser Gly Ile Thr Ile Gly Ile Ile Asp
    130                 135                 140

Thr Gly Ile Asp Ala Ser His Pro Asp Leu Gln Gly Lys Val Ile Gly
145                 150                 155                 160

Trp Val Asp Phe Val Asn Gly Arg Ser Tyr Pro Tyr Asp Asp His Gly
                165                 170                 175

His Gly Thr His Val Ala Ser Ile Ala Ala Gly Thr Gly Ala Ala Ser
            180                 185                 190

Asn Gly Lys Tyr Lys Gly Met Ala Pro Gly Ala Lys Leu Ala Gly Ile
        195                 200                 205

Lys Val Leu Gly Ala Asp Gly Ser Gly Ser Ile Ser Thr Ile Ile Lys
    210                 215                 220

Gly Val Glu Trp Ala Val Asp Asn Lys Asp Lys Tyr Gly Ile Lys Val
225                 230                 235                 240

Ile Asn Leu Ser Leu Gly Ser Ser Gln Ser Ser Asp Gly Thr Asp Ala
                245                 250                 255

Leu Ser Gln Ala Val Asn Ala Ala Trp Asp Ala Gly Leu Val Val Val
            260                 265                 270

Val Ala Ala Gly Asn Ser Gly Pro Asn Lys Tyr Thr Ile Gly Ser Pro
        275                 280                 285

Ala Ala Ala Ser Lys Val Ile Thr Val Gly Ala Val Asp Lys Tyr Asp
    290                 295                 300

Val Ile Thr Ser Phe Ser Ser Arg Gly Pro Thr Ala Asp Gly Arg Leu
305                 310                 315                 320

Lys Pro Glu Val Val Ala Pro Gly Asn Trp Ile Ile Ala Ala Arg Ala
                325                 330                 335

Ser Gly Thr Ser Met Gly Gln Pro Ile Asn Asp Tyr Tyr Thr Ala Ala
            340                 345                 350

Pro Gly Thr Ser Met Ala Thr Pro His Val Ala Gly Ile Ala Ala Leu
        355                 360                 365

Leu Leu Gln Ala His Pro Ser Trp Thr Pro Asp Lys Val Lys Thr Ala
    370                 375                 380

Leu Ile Glu Thr Ala Asp Ile Val Lys Pro Asp Glu Ile Ala Asp Ile
385                 390                 395                 400

Ala Tyr Gly Ala Gly Arg Val Asn Ala Tyr Lys Ala Ile Asn Tyr Asp
                405                 410                 415

Asn Tyr Ala Lys Leu Val Phe Thr Gly Tyr Val Ala Asn Lys Gly Ser
            420                 425                 430

Gln Thr His Gln Phe Val Ile Ser Gly Ala Ser Phe Val Thr Ala Thr
        435                 440                 445

Leu Tyr Trp Asp Asn Ala Asn Ser Asp Leu Asp Leu Tyr Leu Tyr Asp
    450                 455                 460

Pro Asn Gly Asn Gln Val Asp Tyr Ser Tyr Thr Ala Tyr Tyr Asp Phe
465                 470                 475                 480

Glu Lys Val Gly Tyr Tyr Asn Pro Thr Asp Gly Thr Trp Thr Ile Lys
                485                 490                 495

Val Val Ser Tyr Ser Gly Ser Ala Asn Tyr Gln Val Asp Val Val Ser
            500                 505                 510

Asp Gly Ser Leu Ser Gln Pro Gly Ser Ser Pro
```

515 520

<210> SEQ ID NO 3
<211> LENGTH: 333
<212> TYPE: DNA
<213> ORGANISM: Pyrococcus furiosus

<400> SEQUENCE: 3
atggcacctg agaagaaagt tgagcaagtt cgcaacgtag agaaaaacta cggtcttctt 60
acaccaggcc ttttccgcaa aatccaaaaa cttaacccta acgaggagat cagcactgta 120
atcgtttttg agaaccatcg cgagaaggag atcgctgttc gcgttcttga gcttatgggt 180
gcgaaggtac gctacgttta ccatatcatt ccggctattg cggctgacct taaggttcgc 240
gaccttcttg ttatctctgg tcttactggt ggcaaagcga aactttcagg cgttcgcttc 300
atccaagagg actacaaagt tactgtatct taa 333

<210> SEQ ID NO 4
<211> LENGTH: 110
<212> TYPE: PRT
<213> ORGANISM: Pyrococcus furiosus

<400> SEQUENCE: 4

Met Ala Pro Glu Lys Lys Val Glu Gln Val Arg Asn Val Glu Lys Asn
1 5 10 15

Tyr Gly Leu Leu Thr Pro Gly Leu Phe Arg Lys Ile Gln Lys Leu Asn
20 25 30

Pro Asn Glu Glu Ile Ser Thr Val Ile Val Phe Glu Asn His Arg Glu
35 40 45

Lys Glu Ile Ala Val Arg Val Leu Glu Leu Met Gly Ala Lys Val Arg
50 55 60

Tyr Val Tyr His Ile Ile Pro Ala Ile Ala Ala Asp Leu Lys Val Arg
65 70 75 80

Asp Leu Leu Val Ile Ser Gly Leu Thr Gly Gly Lys Ala Lys Leu Ser
85 90 95

Gly Val Arg Phe Ile Gln Glu Asp Tyr Lys Val Thr Val Ser
100 105 110

<210> SEQ ID NO 5
<211> LENGTH: 1269
<212> TYPE: DNA
<213> ORGANISM: Bacillus horneckiae

<400> SEQUENCE: 5
atgaaaaaac cgctggggaa aattgtcgca agcaccgcac tactcatttc tgttgctttt 60
agttcatcga tcgcatcggc taaagataaa gttgaggcaa aggaacaaga ttcatatcgt 120
gtgctaatca aagcaccaac aacatccata agtactttcc aatcaaaata cgatgtccgt 180
tgggattttg gcaaagaggg atttacaaca gatgttgatg ccaaacagct ccaaactctt 240
caaagcaaca aagacattca aattcaaaag gtaaatgaaa ttacagtaga gactgctaca 300
acagatgcaa aaagtacaaa agcggaagtg acggcgacgc caagtacaca aactccttgg 360
ggcataaaat caatttataa tgatcaatca attacaaaaa caactggagg cagcggaatc 420
aaggtagctg tcttagatac aggggttcat acgggccata tagatttagc cggttcttct 480
gagcaatgta aggattttac acaatctaat cctttagtaa atggttcatg tacggatcgc 540
caagggcatg gtacacatgt tgccgggact gtattggcac atgggggcag tgatggacaa 600

```
ggcgtttatg gagtggctcc gcaagcaaaa ctatgggctt ataaagtatt aggtgataac    660

ggcagcggat actctgatga tattgcagcg gctatcagac atgtagccga tgaagcatct    720

cgtacaggtt ccaaagtggt aattaatatg tcgctcggct catctggtaa agattcattg    780

attgctagtg cagtagatta tgcatatgga aaaggtgtct taattgttgc agcggctggc    840

aatagcggat caggaagcaa tacaatcggc tatcctgctg cccttgtaaa tgcagtggca    900

gtagcagcgc tggagaatgt tcagcaaaat ggtacttatc gagtagcaaa tttctcttca    960

agaggaaatc cggcaacagc tggagatttt agaattcaag agcgtgatgt cgaagtttca   1020

gcaccaggtg caagcgtaga gtcaacatgg tacaatggcg gttataatac aatcagcggt   1080

acgtcaatgg caactccaca tgtggccgga ttagcagcta aaatctggtc ttcgaattct   1140

tcattaagtc atagccaact gcgcactgaa ttgcaaaacc gcgctaaagt atatgatatt   1200

aaaggtggta tcggagccgg aacaggtgac gattatgcat cagggttcgg ctatccaaga   1260

gtaaaataa                                                          1269
```

```
<210> SEQ ID NO 6
<211> LENGTH: 422
<212> TYPE: PRT
<213> ORGANISM: Bacillus horneckiae

<400> SEQUENCE: 6

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Lys Asp Lys Val Glu
            20                  25                  30

Ala Lys Glu Gln Asp Ser Tyr Arg Val Leu Ile Lys Ala Pro Thr Thr
        35                  40                  45

Ser Ile Ser Thr Phe Gln Ser Lys Tyr Asp Val Arg Trp Asp Phe Gly
    50                  55                  60

Lys Glu Gly Phe Thr Thr Asp Val Asp Ala Lys Gln Leu Gln Thr Leu
65                  70                  75                  80

Gln Ser Asn Lys Asp Ile Gln Ile Gln Lys Val Asn Glu Ile Thr Val
                85                  90                  95

Glu Thr Ala Thr Thr Asp Ala Lys Ser Thr Lys Ala Glu Val Thr Ala
            100                 105                 110

Thr Pro Ser Thr Gln Thr Pro Trp Gly Ile Lys Ser Ile Tyr Asn Asp
        115                 120                 125

Gln Ser Ile Thr Lys Thr Thr Gly Gly Ser Gly Ile Lys Val Ala Val
    130                 135                 140

Leu Asp Thr Gly Val His Thr Gly His Ile Asp Leu Ala Gly Ser Ser
145                 150                 155                 160

Glu Gln Cys Lys Asp Phe Thr Gln Ser Asn Pro Leu Val Asn Gly Ser
                165                 170                 175

Cys Thr Asp Arg Gln Gly His Gly Thr His Val Ala Gly Thr Val Leu
            180                 185                 190

Ala His Gly Gly Ser Asp Gly Gln Gly Val Tyr Gly Val Ala Pro Gln
        195                 200                 205

Ala Lys Leu Trp Ala Tyr Lys Val Leu Gly Asp Asn Gly Ser Gly Tyr
    210                 215                 220

Ser Asp Asp Ile Ala Ala Ala Ile Arg His Val Ala Asp Glu Ala Ser
225                 230                 235                 240

Arg Thr Gly Ser Lys Val Val Ile Asn Met Ser Leu Gly Ser Ser Gly
                245                 250                 255
```

```
Lys Asp Ser Leu Ile Ala Ser Ala Val Asp Tyr Ala Tyr Gly Lys Gly
            260                 265                 270

Val Leu Ile Val Ala Ala Ala Gly Asn Ser Gly Ser Gly Ser Asn Thr
        275                 280                 285

Ile Gly Tyr Pro Ala Ala Leu Val Asn Ala Val Ala Val Ala Ala Leu
    290                 295                 300

Glu Asn Val Gln Gln Asn Gly Thr Tyr Arg Val Ala Asn Phe Ser Ser
305                 310                 315                 320

Arg Gly Asn Pro Ala Thr Ala Gly Asp Phe Arg Ile Gln Glu Arg Asp
                325                 330                 335

Val Glu Val Ser Ala Pro Gly Ala Ser Val Glu Ser Thr Trp Tyr Asn
            340                 345                 350

Gly Gly Tyr Asn Thr Ile Ser Gly Thr Ser Met Ala Thr Pro His Val
        355                 360                 365

Ala Gly Leu Ala Ala Lys Ile Trp Ser Ser Asn Ser Ser Leu Ser His
    370                 375                 380

Ser Gln Leu Arg Thr Glu Leu Gln Asn Arg Ala Lys Val Tyr Asp Ile
385                 390                 395                 400

Lys Gly Gly Ile Gly Ala Gly Thr Gly Asp Asp Tyr Ala Ser Gly Phe
                405                 410                 415

Gly Tyr Pro Arg Val Lys
            420


<210> SEQ ID NO 7
<211> LENGTH: 249
<212> TYPE: DNA
<213> ORGANISM: Bacillus horneckiae

<400> SEQUENCE: 7

atgaaagata aagttgaggc aaaggaacaa gattcatatc gtgtgctaat caaagcacca      60

acaacatcca taagtacttt ccaatcaaaa tacgatgtcc gttgggattt tggcaaagag     120

ggatttacaa cagatgttga tgccaaacag ctccaaactc ttcaaagcaa caaagacatt     180

caaattcaaa aggtaaatga aattacagta gagactgcta caacagatgc aaaaagtaca     240

aaagcgtaa                                                             249


<210> SEQ ID NO 8
<211> LENGTH: 82
<212> TYPE: PRT
<213> ORGANISM: Bacillus horneckiae

<400> SEQUENCE: 8

Met Lys Asp Lys Val Glu Ala Lys Glu Gln Asp Ser Tyr Arg Val Leu
1               5                   10                  15

Ile Lys Ala Pro Thr Thr Ser Ile Ser Thr Phe Gln Ser Lys Tyr Asp
            20                  25                  30

Val Arg Trp Asp Phe Gly Lys Glu Gly Phe Thr Thr Asp Val Asp Ala
        35                  40                  45

Lys Gln Leu Gln Thr Leu Gln Ser Asn Lys Asp Ile Gln Ile Gln Lys
    50                  55                  60

Val Asn Glu Ile Thr Val Glu Thr Ala Thr Thr Asp Ala Lys Ser Thr
65                  70                  75                  80

Lys Ala
```